US006441262B1

(12) United States Patent
Fung et al.

(10) Patent No.: US 6,441,262 B1
(45) Date of Patent: Aug. 27, 2002

(54) METHOD FOR CONVERTING AN OXYGENATE FEED TO AN OLEFIN PRODUCT

(75) Inventors: Shun C. Fung, Bridgewater, NJ (US); Chunshe Cao, Kennewick, WA (US)

(73) Assignee: ExxonMobil Chemical Patents, Inc., Houston, TX (US)

(*) Notice: Subject to any disclaimer, the term of this patent is extended or adjusted under 35 U.S.C. 154(b) by 0 days.

(21) Appl. No.: 09/785,122

(22) Filed: Feb. 16, 2001

(51) Int. Cl.$^7$ ............................................. C07C 1/207
(52) U.S. Cl. .................. 585/640; 585/638; 585/639; 585/904
(58) Field of Search ................. 585/638, 639, 585/640, 904

(56) References Cited

U.S. PATENT DOCUMENTS

| | | | |
|---|---|---|---|
| 2,768,127 A | 10/1956 | Kimberlin, Jr. et al. ...... | 196/55 |
| 3,258,455 A | 6/1966 | Natta et al. ................ | 260/93.7 |
| 3,305,538 A | 2/1967 | Natta et al. ................ | 260/93.7 |
| 3,364,190 A | 1/1968 | Emrick ...................... | 260/93.7 |
| 3,645,992 A | 2/1972 | Elston ...................... | 260/80.78 |
| 3,785,782 A | 1/1974 | Cartmell .................... | 23/288 |
| 4,035,284 A | 7/1977 | Gross et al. ................ | 208/120 |
| 4,076,698 A | 2/1978 | Anderson et al. ........ | 526/348.6 |
| 4,076,796 A | 2/1978 | Reh et al. .................. | 423/659 |
| 4,134,926 A | 1/1979 | Tsao et al. ................. | 260/682 |
| 4,229,608 A | 10/1980 | Chen et al. ................. | 585/640 |
| 4,243,691 A | 1/1981 | Mohlenkamp, Jr. et al. ......................... | 426/649 |
| 4,251,677 A * | 2/1981 | Coutinho et al. ........... | 585/639 |

(List continued on next page.)

FOREIGN PATENT DOCUMENTS

| | | |
|---|---|---|
| EP | 096 996 | 12/1983 |
| EP | 0 359 841 | 8/1993 |

OTHER PUBLICATIONS

Blackwell et al. Solid–State MNR of Silicoaluminophosphate Molecular Sieves and Aluminophosphate Materials, J. Phys. Chem., vol. 92, pp. 3965–3970 (1988).
Meier et al. Atlas of Zeolite Structural Types, Butterworth Heineman, 4th ed., (1996).
MTO—has its time come? Nitrogen & Methanol, No. 246, (Jul–Aug. 2000).
Barger et al., Converting Natural Gas to Ethylene and Propylene by the UOP/Hydro MTO Process, 12$^{th}$ International Zeolite Conference Materials Research Society p. 567–573 (1999).
Chang, Methanol Conversion to Light Olefins, Catal. Rev.–Sci. Eng., 26(3&4), 323–345 (1984).
Kaeding et al., Production of Chemicals from Methanol, Journal of Catalysis 61, 155–164 (1980).

Primary Examiner—Thuan D. Dang
(74) Attorney, Agent, or Firm—Paul T. Lavoie; Bradley A. Keller

(57) ABSTRACT

The invention provides a method of making ethylene, propylene, and butylene by contacting a molecular sieve catalyst with an oxygenate to convert a portion of the oxygenate to a product containing olefin; separating the catalyst from the olefin product and directing a portion of the separated catalyst to a regenerator; contacting, in an alcohol contact zone, the regenerated catalyst with an alcohol selected from methanol, ethanol, 1-propanol, 1-butanol, or mixtures thereof; and directing the catalyst from the alcohol contact zone to an oxygenate conversion zone. The relative amounts of ethylene, prtoplyene, and butylene produced by the process is in part dependant upon the composition of the alcohol used to contact the regenerated catalyst.

27 Claims, 2 Drawing Sheets

U.S. PATENT DOCUMENTS

| | | | |
|---|---|---|---|
| 4,302,565 A | 11/1981 | Goeke et al. | 526/88 |
| 4,404,095 A | 9/1983 | Haddad et al. | 208/161 |
| 4,419,221 A | 12/1983 | Castagnos, Jr. et al. | 208/113 |
| 4,440,871 A | 4/1984 | Lok et al. | 502/214 |
| 4,499,314 A | 2/1985 | Seddon et al. | 585/408 |
| 4,499,327 A | 2/1985 | Kaiser | 585/640 |
| 4,552,645 A | 11/1985 | Gartside et al. | 208/80 |
| 4,659,685 A | 4/1987 | Coleman, III et al. | 502/113 |
| 4,664,888 A | 5/1987 | Castagnos, Jr. | 422/147 |
| 4,677,242 A | 6/1987 | Kaiser | 585/638 |
| 4,677,243 A | 6/1987 | Kaiser | 585/638 |
| 4,752,651 A | 6/1988 | Kaiser | 585/640 |
| 4,780,196 A | 10/1988 | Alagy et al. | 208/130 |
| 4,814,067 A | 3/1989 | Gartside et al. | 208/127 |
| 4,861,743 A | 8/1989 | Flank et al. | 502/214 |
| 4,861,938 A | 8/1989 | Lewis et al. | 585/640 |
| 5,095,163 A | 3/1992 | Barger | 585/640 |
| 5,096,684 A | 3/1992 | Guth et al. | 423/306 |
| 5,126,308 A | 6/1992 | Barger et al. | 502/214 |
| 5,191,141 A | 3/1993 | Barger et al. | 585/640 |
| 5,343,830 A | 9/1994 | Alexander et al. | 122/4 |
| 5,714,662 A | 2/1998 | Vora et al. | 585/640 |
| 5,714,663 A | 2/1998 | Serrand et al. | 585/648 |
| 5,817,906 A | 10/1998 | Marker et al. | 585/640 |
| 5,892,079 A | 4/1999 | Wilson, Jr. | 556/11 |
| 5,914,433 A | 6/1999 | Marker | 585/313 |
| 5,925,800 A | 7/1999 | Sun et al. | 585/640 |
| 5,952,538 A | 9/1999 | Vaughn et al. | 585/640 |
| 5,972,203 A | 10/1999 | Smith et al. | 208/113 |
| 5,990,369 A | 11/1999 | Barger et al. | 585/640 |
| 6,023,005 A | 2/2000 | Lattner et al. | 585/639 |
| 6,121,503 A | 9/2000 | Janssen et al. | 585/640 |
| 6,121,504 A | 9/2000 | Kuechler et al. | 585/640 |
| 6,137,022 A | 10/2000 | Kuechler et al. | 585/638 |
| 6,166,282 A | 12/2000 | Miller | 585/638 |
| 6,174,339 B1 | 1/2001 | Varady | 55/348 |

\* cited by examiner

METHOD FOR CONVERTING AN OXYGENATE FEED TO AN OLEFIN PRODUCT

FIELD OF THE INVENTION

This invention is directed to a method of converting an oxygenate to an olefin product, particularly ethylene, propylene, and butylene, using a silicoaluminophosphate molecular sieve catalyst.

BACKGROUND OF THE INVENTION

Ethylene is an important petrochemical. In 1998 about 80 million tons of ethylene were produced, and demand is expected to reach 100 million tons by 2003. The primary use for ethylene is as a monomer for the production of low and high density polyethylene. Approximately 60% of world ethylene consumption goes into making polyethylene for such products as plastic films, containers, and coatings. Other uses include the production of vinyl chloride, ethylene oxide, ethylbenzene and alcohols.

Propylene is another important raw material. In 1998 about 46 million tons of propylene were produced, and demand is expected to reach 60 million tons by 2003. About 55% of the world consumption is directed to the production of polypropylene. Other important end products include acrylonitrile for acrylic and nylon fibers, and propylene oxide for polyurethane foams.

Butylenes are useful in preparing a wide variety of derivative end products. Examples of such end products include gasoline alkylate and ethylene-butylene (EB) copolymer. Butylenes are also used as chemical building blocks for larger hydrocarbons. These hydrocarbons find such applications in fuels, lubricants, and specialty chemicals, e.g., plasticizers and solvents.

Ethylene, propylene, and butylene have been traditionally produced by either catalytic or steam cracking of a petroleum feedstock. As the cost of petroleum steadily increases it will be important to find alternative feedstock sources for producing these olefins. Oxygenates are a potential useful alternative to petroleum for producing ethylene and propylene. A particularly promising oxygenate is methanol. Methanol is readily produced from synthesis gas, which is derived from the reforming of natural gas. Large scale production of methanol from "stranded" natural gas could provide methanol at a price that would allow methanol to be economically competitive with petroleum feedstock for the production of ethylene and propylene.

One way in which olefins can be made from an oxygenate feedstock is by catalytic conversion. In U.S. Pat. No. 4,499,327 a catalytic process for converting methanol to olefins is described. The catalyst used in that process contains a silicoaluminophosphate molecular sieve.

It is highly desirable to convert as much of the oxygenate feedstock as possible into as much olefin product as possible. Various methods of doing such have been suggested. For example, U.S. Pat. No. 4,677,242 describes a method of increasing the amount of ethylene and propylene produced from the catalytic conversion of methanol by adding an aromatic diluent to the methanol. The catalyst that is used in the process contains a silicoaluminophosphate molecular sieve. The use of the diluent is said to result in an increase ethylene selectivity. U.S. Pat. No. 4,499,314 also discloses a catalytic process for converting methanol to ethylene and para-xylene. The catalyst that is used is a zeolitic molecular sieve, ZSM-5. Promoters are used to promote either the formation of aromatic products or olefin products. Benzene, toluene and para-xylene are preferred aromatic promoters. Ethylene, propylene and butenes are preferred olefin promoters.

Silicoaluminophosphate molecular sieve catalysts are particularly useful catalysts for making olefins, such as ethylene and propylene, from oxygenate compounds, such as methanol. However, improved process conditions are needed to increase the production of ethylene andlor propylene, as well as butylene if an oxygenate feedstock is to replace or supplement petroleum feedstock for the production of these olefins. Also, because of market demand fluctuations for ethylene, propylene, and butylene, it would be desirable to vary the production ratio of ethylene to propylene to butylene without significant downtime in production.

SUMMARY OF THE INVENTION

The invention is directed to a method for increasing ethylene, propylene, and/or butylene production in an oxygenate to olefin process using molecular sieve catalysts. Catalyst from the regeneration zone, and optionally fresh catalyst, is contacted with an alcohol in an alcohol contact zone prior to contacting the regenerated or fresh catalyst with the oxygenate feedstock. The alcohol is selected from methanol, ethanol, 1-propanol, 1-butanol, or a mixture thereof. The alcohol or mixture of alcohols used in the alcohol contact zone will affect the production ratio of ethylene to propylene to butylene in the olefin product.

The method for increasing ethylene, propylene, and/or butylene production in an oxygenate to olefin process includes contacting a molecular sieve catalyst with an oxygenate, preferably methanol, to convert a portion of the oxygenate to an olefin product; separating the catalyst from the olefin product and directing a portion of the separated catalyst to a regenerator; contacting, in an alcohol contact zone, the regenerated catalyst with an alcohol, selected from the group consisting of ethanol, 1-propanol, 1-butanol and mixtures thereof; and directing the alcohol contacted catalyst from the alcohol contact zone to an oxygenate conversion zone. The method may further include separating hydrocarbon produced in the alcohol contact zone from the alcohol contacted catalyst, and adding fresh catalyst to the alcohol contact zone. The molecular sieve catalyst used in the invention contains SAPO molecular sieve selected from SAPO-5, SAPO-17, SAPO-18, SAPO-20, SAPO-34, SAPO44, SAPO-56, the metal containing forms of each thereof, or mixtures thereof. Desirably, the temperature of the alcohol contact zone will be about 350° C. to about 550° C. Preferably, the alcohol contact zone is an auxiliary reactor.

The present invention will be better understood by reference to the Detailed Description of the Invention when taken together with the attached drawings and the appended claims.

DETAILED DESCRIPTION OF THE INVENTION

Figure 1:
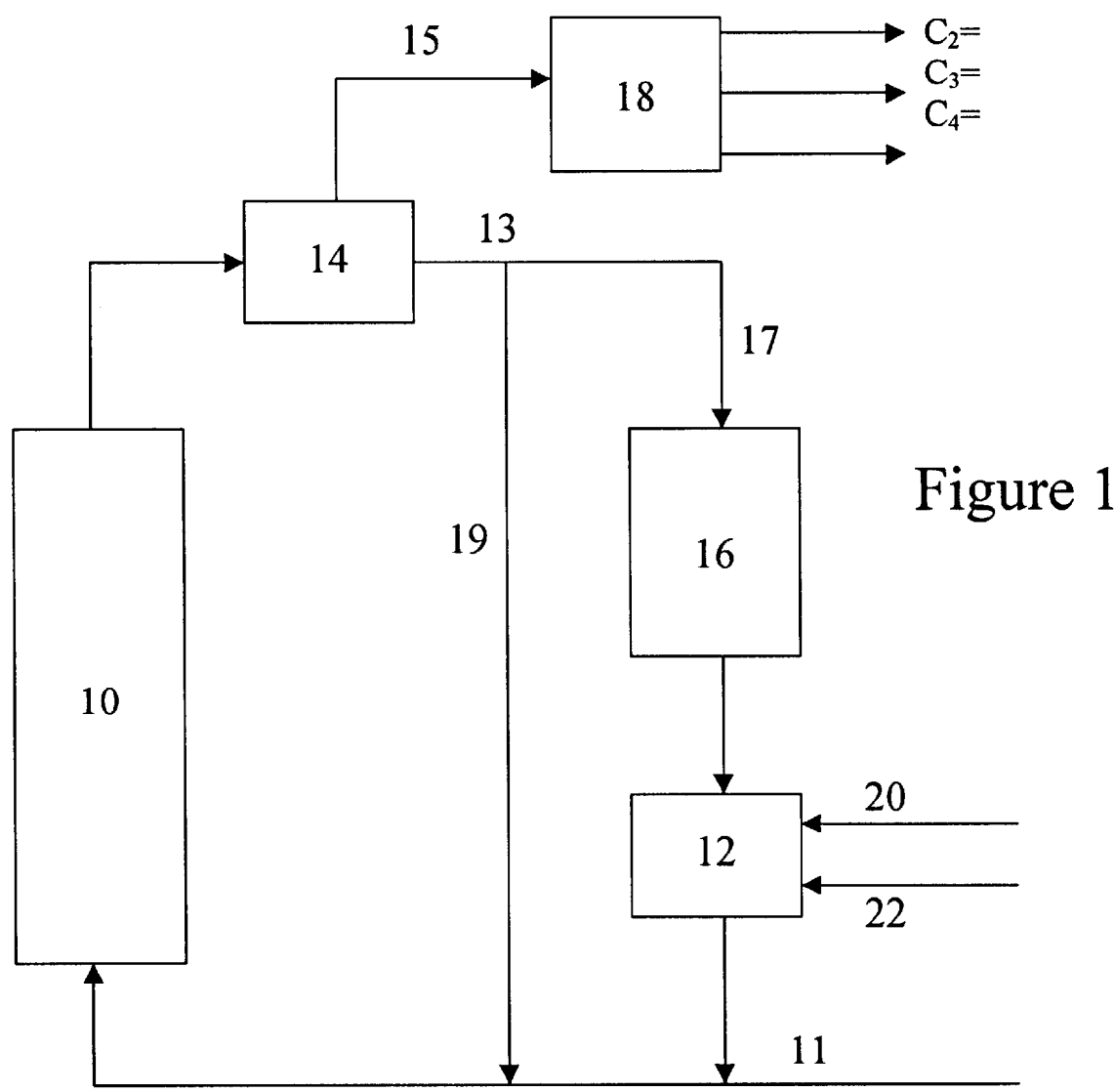
FIG. 1 is a flow diagram of an embodiment of the process of this invention.

This invention is directed to method of making ethylene, propylene, and butylene from an oxygenate feed. The invention provides the ability to vary the production ratio of ethylene to propylene to butylene in an oxygenate to olefinconversion process. The ability to vary this production ratio is important given the tight market dynamics of ethylene, propylene, and butylene demand. For example, if the spot demand for propylene is high, the process can be altered to produce additional propylene. Conversely, if the spot demand for ethylene is high, additional ethylene can be produced. The production ratio of ethylene to propylene to butylene can be adjusted with little, if any, downtime in production. No catalyst change is required and very little, if any, change in operating conditions is required.

The invention provides a process for increasing the production of ethylene, pfoplyene, and/or butylene by contacting all or a portion of regenerated catalyst with an alcohol feed in an alcohol contact zone prior to directing the regenerated catalyst to an oxygenate conversion zone. Fresh catalyst may also be directed to the alcohol contact zone prior to contacting the oxygenate feed. Fresh catalyst is defined as catalyst that has yet to contact oxygenate in an oxygenate conversion reactor. Regenerated catalyst is defined as catalyst that has contacted oxygenate in an oxygenate conversion reactor and has passed through a regenerator to remove carbonaceous material from the catalyst.

In the alcohol contact zone regenerated or fresh catalyst contacts an alcohol feed. The alcohol feed contains one or more alcohols selected from ethanol, 1-propanol, 1-butanol, or a mixture thereof. The alcohol feed may also contain methanol. Preferably, to optimize the production of ethylene, the alcohol feed will contain greater than about 70% by weight ethanol. Other embodiments include an alcohol feed that contains from about 1% to about 90% by weight methanol and from about 1% to about 99% by weight ethanol. Preferably, the alcohol feed will contain from about 1% to about 60% by weight methanol and from about 40% to about 99% by weight ethanol, more preferably from about 1% to about 30% by weight methanol and from about 70% to about 99% by weight ethanol.

A portion of the ethanol that contacts the catalyst is converted to olefin, primarily to ethylene. In the alcohol contact zone, greater than about 85%, preferably greater than about 95% of the ethanol is converted to ethylene. As a result, the ethylene produced in the alcohol contact zone adds to the overall ethylene productivity. The alcohol-contacted catalyst is then directed to the oxygenate conversion reactor. The olefin product produced in the alcohol contact zone is also directed to the oxygenate conversion reactor. Alternatively, a portion of the olefin product produced in the alcohol contact zone may be separated from the alcohol-contacted catalyst prior to the catalyst being fed into the oxygenate conversion reactor.

Preferably, to optimize the production of propylene, the alcohol feed to the alcohol contact zone will contain greater than about 70% by weight 1-propanol. In other instances it may be desirable to use a 1-propanol/methanol mixture as the alcohol feed. The alcohol feed will contain from about 1% to about 90% by weight methanol and from about 1% to about 99% by weight 1-propanol. Preferably, the alcohol feed will contain from about 1% to about 60% by weight methanol and from about 40% to about 99% by weight 1-propanol, more preferably from about 1% to about 30% by weight methanol and from about 70% to about 99% by weight 1-propanol. A portion of the 1-propanol that contacts the catalyst is converted to olefin, primarily to propylene. In the alcohol contact zone, about 70% to about 85% of the 1-propanol is converted to propylene, and about 10% to about 25% is converted to butenes and pentenes, which are also commercially valued olefins.

Preferably, to optimize the production of butylene, the alcohol feed to the alcohol contact zone will contain greater than about 70% by weight 1-butanol. In other instances it may be desirable to use a 1-butanol-methanol mixture as the alcohol feed. The alcohol feed will contain from about 1% to about 90% by weight methanol and from about 1% to about 99% by weight 1-butanol. Preferably, the alcohol feed will contain from about 1% to about 60% by weight methanol and from about 40% to about 99% by weight 1-butanol, more preferably from about 1% to about 30% by weight methanol and from about 70% to about 99% by weight 1-butanol. A portion of the 1-butanol that contacts the catalyst is converted to olefin, primarily to butylene. In the alcohol contact zone, about 40% to about 60% of the 1-butanol is converted to butylene, about 20% to about 30% is converted to propylene, and about 10% to about 20% is converted to pentenes, which are also commercially valued olefins.

The alcohol feed to the alcohol contact zone may also contain mixtures of methanol, ethanol, 1-propanol, and 1-butanol. For example, the alcohol feed may contain from about 1% to about 90% by weight methanol, from about 5% to about 90% by weight ethanol, from about 5% to about 90% by weight 1-propanol, and from about 5% to about 90% by weight 1-butanol. The greater the proportion of ethanol in the alcohol feed results in additional ethylene in the olefin product. Conversely, a greater proportion of 1-propanol in the alcohol feed results in additional propylene in the olefin product. It may also be desirable to feed a mixture of ethanol and 1-propanol to the alcohol contact zone to increase the overall production of both ethylene and propylene in the olefin product. Likewise, greater amounts of 1-butanol and 1-propanol in the alcohol feed will increase the overall production of propylene and butylene in the olefin product.

The amount of alcohol feed added to the alcohol contact zone can vary from about 2% to about 60% by weight $CH_2$ per weight of regenerated and fresh catalyst added to the alcohol contact zone. Preferably the amount of alcohol feed added will vary from about 2% to about 20% by weight $CH_2$ per weight catalyst. More preferably the amount of alcohol feed added will vary from about 4% to about 12% by weight $CH_2$ per weight catalyst. Methanol contains one $CH_2$ group or 44% by weight $CH_2$. Ethanol contains two $CH_2$ groups or 61% by weight $CH_2$. 1-propanol contains three $CH_2$ groups or 70% by weight $CH_2$. 1-butanol contains four $CH_2$ groups or 76% by weight $CH_2$. Accordingly, the alcohol feed will contain sufficient amounts of $CH_2$ to satisfy the catalyst feed to the alcohol contact zone for each of the stated ranges.

The alcohol feed in the alcohol contact zone may also contain one or more inert diluents. As defined herein, diluents are compositions which are essentially non-reactive across a molecular sieve catalyst, and primarily function to make the alcohol feed less concentrated. Typical diluents include, but are not necessarily limited to, helium, argon, nitrogen, carbon monoxide, carbon dioxide, water, paraffins (especially the alkanes such as methane, ethane, and propane), aromatic compounds,. and mixtures thereof. The preferred diluents are water and nitrogen. Water can be injected in either liquid or vapor form.

It is to be understood that due to the hydroscopic nature of methanol, ethanol, 1-propanol, and 1-butanol, water may be contained within these alcohols without significantly affecting the advantages of the invention. The amount of water or the diluents in the alcohol feed is exclusive of the stated weight percent ranges of the alcohols in the alcohol feed.

The oxygenate feedstock to the oxygenate conversion reactor of this invention comprises at least one organic compound which contains at least one oxygen atom, e.g., the lower alcohols, ethers, ketone, and mixtures thereof. Examples of suitable oxygenate compounds include, but are not limited to: methanol; ethanol; 1-propanol; dimethylether; acetone; and mixtures thereof. Preferred oxygenate compounds are methanol, dimethylether, or a mixture thereof. The oxygenate, preferably methanol, is added at one or more points to the oxygenate conversion reactor and/or to the catalyst feed from the alcohol contact zone. The oxygenate is converted to a product containing olefin.

One or more inert diluents and/or hydrocarbons may also be present in the oxygenate feedstock. As defined herein, hydrocarbons included with the feedstock are hydrocarbon compositions which are converted to another chemical arrangement when contacted with molecular sieve catalyst. These hydrocarbons can include olefins, reactive paraffins, reactive alkylaromatics, reactive aromatics or mixtures thereof. Preferred hydrocarbon co-feeds include, propylene, butylene, pentylene, $C_4^+$ hydrocarbon mixtures, $C_5^+$ hydrocarbon mixtures, and mixtures thereof. More preferred as co-feeds are $C_4^+$ hydrocarbon mixtures, with the most preferred being $C_4^+$ hydrocarbon mixtures which are obtained from separation and recycle of reactor product.

In the preferred embodiment, an auxiliary reactor is used as the alcohol contact zone. Preferably, the auxiliary reactor is physically separated from the oxygenate conversion reactor. Desirably, the auxiliary reactor is a fluidized bed reactor operationally positioned between the oxygenate conversion reactor and the regenerator. The auxiliary reactor is capable of continuously receiving catalyst from the regenerator and subsequently supplying the alcohol contacted catalyst to the conversion reactor. The auxiliary reactor is also capable of continuously receiving fresh catalyst.

Generally, when the alcohol contact zone is an auxiliary reactor, the temperature of the auxiliary reactor will be less than the temperature of the oxygenate conversion reactor. Preferably, the temperature of the auxiliary reactor is 50° C. less than, more preferably 80° C. less than, most preferably 10° C. less than, the temperature of the oxygenate conversion reactor. In a preferred embodiment, the temperature in the alcohol contact zone is from about 150° C. to about 500° C., more preferably from about 200° C. to about 400° C., most preferably from about 250° C. to about 350° C.

Alternatively, an alcohol contact zone in the oxygenate conversion reactor may substitute for the auxiliary reactor. The oxygenate conversion reactor would then comprise an oxygenate conversion zone and a contact zone. The function of the alcohol contact zone in the oxygenate conversion reactor is nearly identical to that of the auxiliary reactor. Generally, the temperature of the alcohol contact zone is less than the temperature in the oxygenate conversion zone of the reactor. Preferably, the temperature of the alcohol contact zone is about 50° C. less than, more preferably about 80° C. less than, most preferably about 100° C. less than, the temperature of the oxygenate conversion zone. In a preferred embodiment, the temperature in the alcohol contact zone is from about 150° C. to about 500° C., more preferably from about 200° C. to about 400° C., most preferably from about 250° C. to about 350° C.

The alcohol feed contacts regenerated catalyst, and optionally fresh catalyst, in the contact zone at a pressure from about 20 psia to about 1000 psia. Preferably, the alcohol feed contacts the catalyst at a pressure from about 25 psia to about 500 psia, more preferably at a pressure from about 30 psia to about 200 psia.

The alcohol feed contacts regenerated catalyst, and optionally fresh catalyst, at a weight hour space velocity (WHSV) from about 1 $hr^{-1}$ to about 500 $hr^{-1}$. Preferably, the alcohol feed contacts the catalyst at WHSV from about 1 $hr^{-1}$ to about 100 $hr^{-1}$, more preferably at a WHSV from about 1 $hr^{-1}$ to about 50 $hr^{-1}$. WHSV is defined herein as the weight of oxygenate feed or alcohol feed, and/or hydrocarbon which may optionally be in the feed, per hour per weight of the molecular sieve content of the catalyst. Because the catalyst or the feed may contain other materials which act as inerts or diluents, the WHSV is calculated on the weight basis of the oxygenate or alcohol feed, and any hydrocarbon which may be present, and the molecular sieve contained in the catalyst.

The catalyst that is used in this invention is one that incorporates a SAPO molecular sieve. The SAPO molecular sieve contains a three-dimensional microporous crystal framework structure of $[SiO_2]$, $[AlO_2]$ and $[PO_2]$ corner sharing tetrahedral units. The way Si is incorporated into the structure can be determined by $^{29}Si$ MAS NMR. See Blackwell and Patton, *J. Phys. Chem.*, 92, 3965 (1988). The desired SAPO molecular sieves will exhibit one or more peaks in the $^{29}Si$ MAS NMR, with a chemical shift $\delta(Si)$ in the range of −88 to −96 ppm and with a combined peak area in that range of at least 20% of the total peak area of all peaks with a chemical shift $\delta(Si)$ in the range of −88 ppm to −115 ppm, where the $\delta(Si)$ chemical shifts refer to external tetramethylsilane (TMS).

It is preferred that the silicoaluminophosphate molecular sieve used in this invention have a relatively low $Si/Al_2$ ratio. In general, the lower the $Si/Al_2$ ratio, the lower the $C_1$–$C_4$ saturates selectivity, particularly propane selectivity. A $Si/Al_2$ ratio of less than 0.65 is desirable, with a $Si/Al_2$ ratio of not greater than 0.40 being preferred, and a $Si/Al_2$ ratio of not greater than 0.32 being particularly preferred. A $Si/Al_2$ ratio of not greater than 0.20 is most preferred.

Silicoaluminophosphate molecular sieves are generally classified as being microporous materials having 8, 10, or 12 membered ring structures. These ring structures can have an average pore size ranging from about 3.5 angstroms to about 15 angstroms. Preferred are the small pore SAPO molecular sieves having an average pore size of less than about 5 angstroms, preferably an average pore size ranging from about 3.5 angstroms to about 5 angstroms, more preferably from about 3.5 angstroms about to 4.2 angstroms. Particularly, the molecular sieve used in conjunction with this invention will have 8 membered rings.

In general, silicoaluminophosphate molecular sieves comprise a molecular framework of corner-sharing $[SiO_2]$, $[AlO_2]$, and $[PO_2]$ tetrahedral units. This type of framework is effective in converting various oxygenates into olefin products.

The $[PO_2]$ tetrahedral units within the framework structure of the molecular sieve of this invention can be provided by a variety of compositions. Examples of these phosphorus-containing compositions include phosphoric acid, organic phosphates such as triethyl phosphate, and aluminophosphates. The phosphorous-containing compositions are mixed with reactive silicon and aluminum-containing compositions under the appropriate conditions to form the molecular sieve.

The $[AlO_2]$ tetrahedral units within the framework structure can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to form the molecular sieve.

The [SiO$_2$] tetrahedral units within the framework structure can be provided by a variety of compositions. Examples of these silicon-containing compositions include silica sols and silicium alkoxides such as tetra ethyl orthosilicate. The silicon-containing compositions are mixed with reactive aluminum and phosphoruscontaining compositions under the appropriate conditions to form the molecular sieve.

Substituted SAPOs can also be used in this invention. These compounds are generally known as MeAPSOs or metal-containing silicoaluminophosphates. The metal can be alkali metal ions (Group IA), alkaline earth metal ions (Group IIA), rare earth ions (Group IIIB, including the lanthanide elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIIB, VIIIB, and IB.

Preferably, !he Me represents atoms such as Zn, Mg, Mn, Co, Ni, Ga, Fe, Ti, Zr, Ge, Sn, and Cr. These atoms can be inserted into the tetrahedral framework through a [MeO$_2$] tetrahedral unit. The [MeO$_2$] tetrahedral unit carries a net electric charge depending on the valence state of the metal substituent. When the metal component has a valence state of +2, +3, +4, +5, or +6, the net electric charge is between −2 and +2. Incorporation of the metal component is typically accomplished adding the metal component during synthesis of the molecular sieve. However, post-synthesis ion exchange can also be used.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO40, SAPO41, SAPO-42, SAPO-44, SAPO-47, SAPO-56, the metal containing forms thereof, and mixtures thereof. Preferred are SAPO-17, SAPO-18, SAPO-34, SAPO-44, SAPO-47, and SAPO-56, particularly SAPO-17, SAPO-18 and SAPO-34, including the metal containing forms thereof, and mixtures thereof. As used herein, the term mixture is synonymous with combination and is considered a composition of matter having two or more components in varying proportions, regardless of their physical state.

The silicoaluminophosphate molecular sieves are synthesized by hydrothermal crystallization methods generally known in the art. See, for example, U.S. Pat. Nos. 4,440,871; 4,861,743; 5,096,684; and 5,126,308. A reaction mixture is formed by mixing together reactive silicon, aluminum and phosphorus components, along with at least one template. Generally the mixture is sealed and heated, preferably under autogenous pressure, to a temperature of at least 100° C., preferably from 100° C. to 250° C., until a crystalline product is formed. Formation of the crystalline product can take anywhere from around 2 hours to as much as 2 weeks. In some cases, stirring or seeding with crystalline material will facilitate the formation of the product.

Typically, the molecular sieve product will be formed in solution. It can be recovered by standard means, such as by centrifugation or filtration. The product can also be washed, recovered by standard means, and dried.

As a result of the crystallization process, the recovered sieve contains within its pores at least a portion of the template used in making the initial reaction mixture. The crystalline structure essentially wraps around the template, and the template must be removed so that the molecular sieve can exhibit catalytic activity. Once the template is removed, the crystalline structure that remains has what is typically called an intracrystalline pore system.

In many cases, depending upon the nature of the final product formed, the template may be too large to be eluted from the intracrystalline pore system. In such a case, the template can be removed by a heat treatment process. For example, the template can be calcined, or essentially combusted, in the presence of an oxygen-containing gas, by contacting the template-containing sieve in the presence of the oxygen-containing gas and heating at temperatures from 200° C. to 900° C. In some cases, it may be desirable to heat in an environment having a low oxygen concentration. In these cases, however, the result will typically be a breakdown of the template into a smaller molecular fragments, rather than by combustion. This type of process can be used for partial or complete removal of the template from the intracrystalline pore system. In other cases, with smaller templates, complete or partial removal from the sieve can be accomplished by conventional desorption processes such as those used in making standard zeolites.

The reaction mixture can contain one or more templates. Templates are structure- directing or affecting agents, and typically contain nitrogen, phosphorus, oxygen, carbon, hydrogen or a combination thereof, and can also contain at least one alkyl or aryl group, with 1 to 8 carbons being present in the alkyl or aryl group. Mixtures of two or more templates can produce mixtures of different sieves or predominantly one sieve where one template is more strongly directing than another.

Representative templates include tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine and combinations thereof. Preferred templates are triethylamine, cyclohexylamine, piperidine, pyridine, isopropylamine, tetraethyl ammonium salts, dipropylamine, and mixtures thereof. The tetraethylammonium salts include tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate. Preferred tetraethyl ammonium salts are tetraethyl ammonium hydroxide and tetraethyl ammonium phosphate.

The SAPO molecular sieve structure can be effectively controlled using combinations of templates. For example, in a particularly preferred embodiment, the SAPO molecular sieve is manufactured using a template combination of TEAOH and dipropylamine. This combination results in a particularly desirable SAPO structure for the conversion of oxygenates, particularly methanol and dimethyl ether, to light olefins such as ethylene and propylene.

The silicoaluminophosphate molecular sieve is typically admixed (i.e., blended) with other materials. When blended, the resulting composition is typically referred to as a SAPO catalyst, with the catalyst comprising the SAPO molecular sieve.

Materials which can be blended with the molecular sieve can be various inert or catalytically active materials, or various binder materials. These materials include compositions such as kaolin and other clays, various forms of rare earth metals, metal oxides, other non-zeolite catalyst components, zeolite catalyst components, alumina or alumina sol, titania, zirconia, magnesia, thoria, beryllia, quartz, silica or silica or silica sol, and mixtures thereof. These components are also effective in reducing, inter alia, overall catalyst cost, acting as a thermal sink to assist in heat shielding the catalyst during regeneration, densifying the catalyst and increasing catalyst strength. It is particularly desirable that the inert materials that are used in the catalyst to act as a thermal sink have a heat capacity of from about 0.05 cal/g-° C. to about 1 cal/g-° C., more preferably from about 0.1 cal/g-°C. to about 0.8 cal/g-°C., most preferably from about 0.1 cal/g-°C. to about 0.5 cal/g-°C.

Additional molecular sieve materials can be included as a part of the SAPO catalyst composition or they can be used as separate molecular sieve catalysts in admixture with the SAPO catalyst if desired. Structural types of small pore molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof. Structural types of medium pore molecular sieves that are suitable for use in this invention include MFI, MEL, MTW, EUO, MUT, HEU, FER, AFO, AEL, TON,.and substituted forms thereof. These small and medium pore molecular sieves are described in greater detail in the *Atlas of Zeolite Structural Types*, W. M. Meier and D. H. Olsen, Butterworth Heineman, 3rd ed., 1997. Preferred molecular sieves which can be combined with a silicoaluminophosphate catalyst include ZSM-5, ZSM-34, erionite, and chabazite.

The catalyst composition preferably comprises about 1% to about 99%, more preferably about 5% to about 90%, and most preferably about 10% to about 80%, by weight of molecular sieve. It is also preferred that the catalyst composition have a particle size of from about 20 $\mu$m to about 3,000 $\mu$m, more preferably about 30 $\mu$m to about 200 $\mu$m, most preferably about 50 $\mu$m to about 150 $\mu$m.

Olefin product can be separated from catalyst using conventional means. For example, conventional cyclones or other separation devices can be used to separate the olefin product from the contacted catalyst. Following separation a portion of the contacted catalyst is directed back to the methanol feed, and a portion of the catalyst is directed to a regenerator for coke removal.

As the catalyst is exposed to the oxygenate, carbonaceous material known as coke accumulates within the pores of the molecular sieve. This coke leads to a partial deactivation of the catalyst. As a result, the coke must be removed by contacting the catalyst with a regeneration medium. In the invention, a portion of oxygenate exposed catalyst is regenerated by contacting the oxygenate exposed catalyst with a regeneration medium to remove all or part of the coke deposits that accumulate within the pores of the molecular sieve.

Any standard oxygenate conversion reactor system can be used, including fixed bed, fluid bed or moving bed systems. Preferred reactors are co-current riser reactors and short contact time, countercurrent free-fall reactors in which an oxygenate feedstock can be contacted with a molecular sieve catalyst at a WHSV of at least about 1 hr$^{-1}$, preferably in the range of from about 20 hr$^{-1}$ to about 1000 hr$^{-1}$, and most preferably in the range of from about 20 hr$^{-1}$ to about 500 hr$^{-1}$.

Preferably, the oxygenate feed, as well as the alcohol feed, contacts the catalyst in the vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

The oxygenate conversion process can generally be carried out at a wide range of temperatures. An effective operating temperature range can be from about 200° C. to about 700° C., preferably from about 300° C. to about 600° C., more preferably from about 350° C. to about 550° C. At the lower end of the temperature range, the formation of the desired olefin products may become markedly slow. At the upper end of the temperature range, the process may not form an optimum amount of product.

The pressure throughout the system also may vary over a wide range, including autogenous pressures. Effective pressures may be in, but are not necessarily limited to, oxygenate partial pressures at least 1 psia, preferably at least 5 psia. The process is particularly effective at higher oxygenate partial pressures, such as an oxygenate partial pressure of greater than 20 psia. Preferably, the oxygenate partial pressure is at least about 25 psia, more preferably at least about 30 psia. For practical design purposes it is desirable to operate at a methanol partial pressure of not greater than about 500 psia, preferably not greater than about 400 psia, most preferably not greater than about 300 psia.

It is desirable to strip at least some of the volatile organic components which may be adsorbed onto the catalyst or located within its microporous structure prior to entering the regenerator. This can be accomplished by passing a stripping gas over the catalyst in a stripper or stripping chamber, which can be located within the reactor or in a separate vessel. The stripping gas can be any substantially inert medium that is commonly used. Examples of stripping gas are steam, nitrogen, helium, argon, methane, $CO_2$, CO, flue gas, and hydrogen.

It is desirable in this invention that the catalyst within the conversion reactor be maintained at a condition optimized for the selectivity to ethylene and/or propylene. It is desirable to maintain the catalyst within the reactor at an average carbon content of from about 1.0% to about 25% by weight, more preferably from about 2% to about 15% by weight. In order to maintain this average level of carbon on catalyst, a portion of the catalyst that has been separated from the olefin product is directed to a regenerator. The portion of catalyst to be regenerated is preferably regenerated under conditions effective to obtain a regenerated catalyst having a carbon content of less than 2 wt. %, preferably less than 1.5 wt. %, and most preferably less than 1.0 wt. %.

In the regenerator, the catalyst is contacted with a regeneration medium containing oxygen or other oxidants. Examples of other oxidants include $O_3$, $SO_3$, $N_2O$, NO, $NO_2$, $N_2O_5$, and mixtures thereof. It is preferred to supply $O_2$ in the form of air. The air can be diluted with nitrogen, $CO_2$; or flue gas, and steam may be added. Desirably, the $O_2$ concentration in the regenerator is reduced to a controlled level to minimize overheating or the creation of hot spots in the spent or deactivated catalyst. The deactivated catalyst also may be regenerated reductively with $H_2$, CO, mixtures thereof, or other suitable reducing agents. A combination of oxidative regeneration and reductive regeneration can also be employed.

The coke deposits are removed from the catalyst during the regeneration process, forming a regenerated catalyst. Typical regeneration temperatures are from 250° C. to 700° C., desirably from 350° C. to 700° C. Preferably, regeneration is carried out at a temperature of 450° C. to 700° C. It may be desirable to cool at least a portion of the regenerated catalyst to a lower temperature before it is directed to the alcohol contact zone. A heat exchanger located externally to the regenerator may be used to remove some heat from. the catalyst after it has been withdrawn from the regenerator.

A preferred embodiment of the oxygenate to olefin conversion process is shown in FIG. 1, with the reaction being carried out in an oxygenate conversion reactor 10. Oxygenate is introduced into the process through line 11. The oxygenate contacts catalyst from the alcohol contact zone 12, which is shown in FIG. 1 as an auxiliary reactor. The mix of catalyst from the alcohol contact zone 12 and oxygenate enters reactor 10 where the oxygenate is converted to olefin product. Catalyst that has bypassed the regenerator 16 is also added to the oxygenate via line 19. Some conversion to olefin may also occur prior to entering the reactor 10 because the catalyst from the auxiliary reactor is at an elevated temperature when it contacts the oxygenate from line 11.

Any unreacted. feed and/or product formed is separated from the catalyst in separator 14 by a appropriate filtering or separation means. Any conventional separation means, e.g., cyclone separators or filters, can be used. Cyclone separators are preferred. The catalyst preferably flows downward from separator 14, forming a dense, fluidized bed. The catalyst is then removed through line 13. Hydrocarbon product from separator 14 is removed through line 15. Conventional separation means 18, such as ethylene and propylene fractionation units, are used to separate the desired olefins from the hydrocarbon product. Additional separation units may be utilized to remove various oxygenates, e.g., dimethyl ether, from the hydrocarbon product.

A portion of the catalyst from separator 14 is sent to regenerator 16 via line 17, where oxidation of the coke takes place. Any conventional regeneration means can be used. Once oxidation is sufficiently complete, the regenerated catalyst is directed to the alcohol contact zone 12. In the auxiliary reactor the regenerated catalyst contacts the alcohol feed 20. Fresh catalyst 22 may also be introduced to the alcohol contact zone 12.

One skilled in the art will also appreciate that the olefins produced by the oxygenate to olefin conversion reaction of the present invention can be polymerized to form polyolefins, particularly polyethylene and polypropylene. Processes for forming polyolefins from olefins are known in the art. Catalytic processes are preferred. Particularly preferred are metallocene, Ziegler/Natta and acid catalytic systems. See, for example, U.S. Pat. Nos. 3,258,455; 3,305, 538; 3,364,190; 5,892,079; 4,659,685; 4,076,698; 3,645, 992; 4,302,565; and 4,243,691. In general, these methods involve contacting the olefin product with a polyolefin-forming catalyst at a pressure and temperature effective to form the polyolefin product.

A preferred polyolefin-forming catalyst is a metallocene catalyst. The preferred temperature range of operation is from 50° C. to 240° C. and the reaction can be carried out at low, medium or high pressure, being anywhere from about 1 bar to 200 bars. For processes carried out in solution, an inert diluent can be used, and the preferred operating pressure is from 10 bars to 150 bars, with a preferred temperature from 120° C. to 230° C. For gas phase processes, it is preferred that the temperature generally be within a temperature of 60° C. to 160° C., and that the operating pressure be from 5 bars to 50 bars.

In addition to polyolefins, numerous other olefin derivatives may be formed from the olefins recovered therefrom. These include, but are not limited to, aldehydes, alcohols, acetic acid, linear alpha olefins, vinyl acetate, ethylene dicholoride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes. The methods of manufacturing these derivatives are well known in the art, and therefore, are not discussed herein.

This invention will be better understood with reference to the following examples, which are intended to illustrate specific embodiments within the overall scope of the invention as claimed.

EXAMPLE 1

SAPO-34 catalyst, 0.3 g, 50% SAPO-34/50% binder, was added to a fluidized-batch-recirculating (FBR) reactor at a gas-recirculating rate of about 10 circulations per second. The catalyst was placed in a basket bound by two sintered-porous metal disks. An impeller rotating at 6000–7000 rpm circulated the gas in the reactor from the top of the basket through the annulus space to the bottom of the basket. The gas entered the bottom of the basket at a speed sufficient to fluidize the catalyst particles. Catalyst particles were in turbulent fluidization condition with very limited amount of gas bubbles in the suspension. Gas residence time was controlled by time-programmed valves that emptied the reactor gas to a large vacuum vessel. A gas chromatograph (GC) sampling valve was used to collect a gas sample for product composition analysis.

The reactor was maintained at a temperature of about 450° C. A pressure of about 60 psia was maintained by adding sufficient quantities of argon. This was to ensure that the circulation of the argon gas by the fast rotation of the impeller can fluidize the catalyst particles before the injection of 0.07 cm$^3$ methanol so that there are good contacts of the oxygenates with the fluidized catalyst particles. The 0.07 cm$^3$ methanol provides a feed to catalyst ratio (based on $CH_2$ content in the oxygenate) of 0.08/1. The reaction time was controlled by venting the reactor gas, via an automated valve, passing a GC sampling valve to a vacuum vessel at a preset time of one minute. The gas composition was determined by GC analysis and is shown in Table 1 which provides conversion and selectivity data.

EXAMPLE 2

An experiment identical to Example 1 was conducted using 0.05 cm$^3$ of ethanol instead of methanol. The lower amount of ethanol used as compared with methanol is to account for their density difference and molecular weight difference. They both give a feed to catalyst ratio (based on $CH_2$ content in the oxygenates) of 0.08/1. Table 1 shows the conversion and selectivity data for ethanol conversion.

EXAMPLE 3

Figure 2:
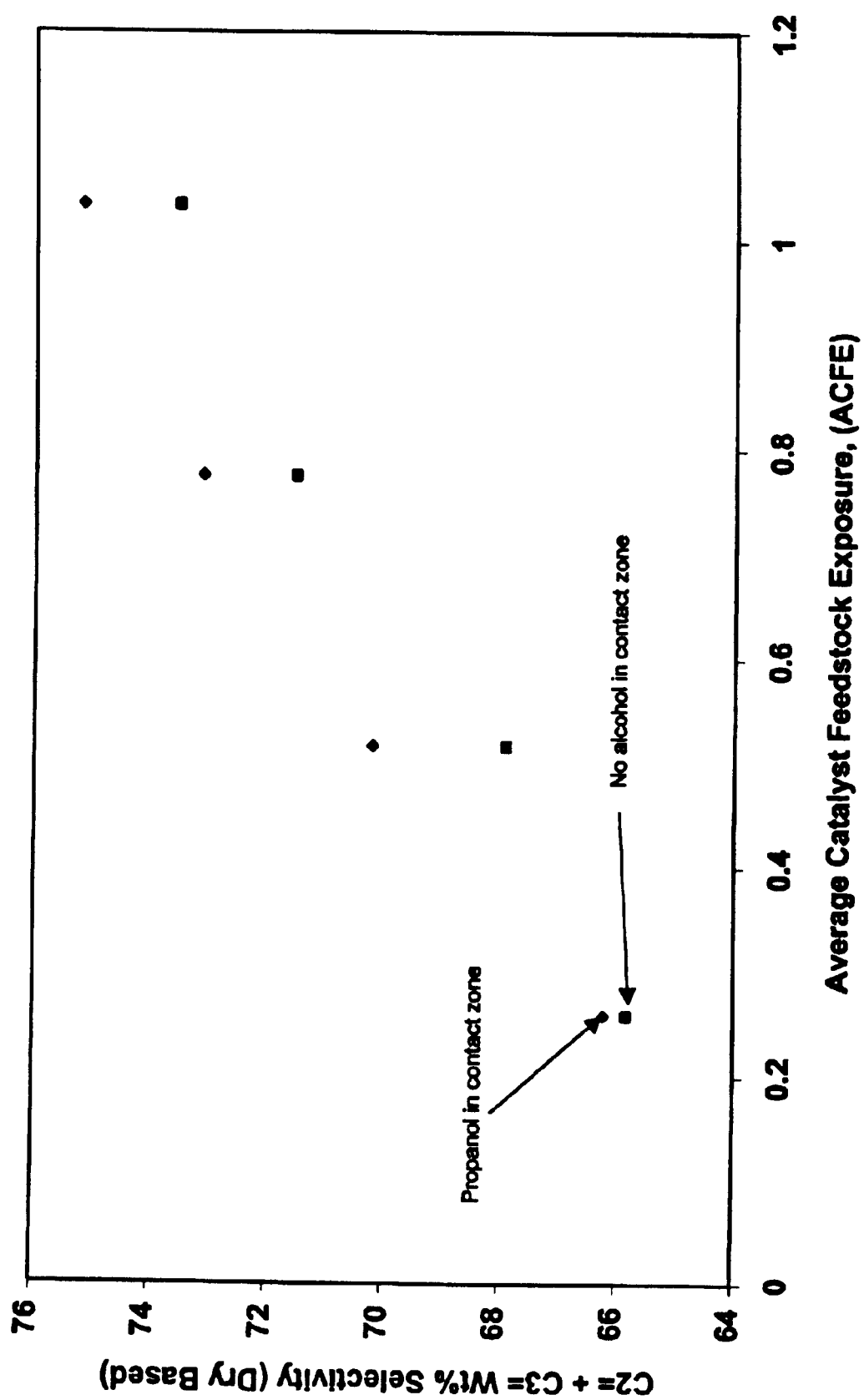
FIG. 2 is a graph of ethylene and propylene selectivity for catalyst contacted with propanol.

An experiment identical to Example 1 was conducted using 0.043 cm$^3$ of 1-propanol instead of methanol. The lower amount of 1-propanol used as compared with methanol is to account for their density difference and molecular weight difference. They both give a feed to catalyst ratio (based on $CH_2$ content in the oxygenates) of 0.08/1. Table 1 shows the conversion and selectivity data for 1-propanol conversion. FIG. 2 shows the higher ethylene and propylene selectivity for fresh catalyst contacted with propanol.

EXAMPLE 4

An experiment identical to Example 1 was conducted using 0.04 cm$^3$ of 1-butanol instead of methanol. The lower amount of 1-butanol used as compared with methanol is to account for their density difference and molecular weight difference. They both give a feed to catalyst ratio (based on $CH_2$ content in the oxygenates) of 0.08/1. Table 1 shows the conversion and selectivity data for 1-butanol conversion.

Table 1 indicates that fresh SAPO catalyst contacted with ethanol, 1-propanol, or 1-butanol in an alcohol contact zone possess relatively higher rates of methanol conversion and higher ethylene, propylene, and butylene selectivity, respectively, than SAPO catalyst contacted with methanol under similar reaction conditions. Ethanol and 1-propanol produce much higher $C_2$=plus $C_3$=selectivities, 99% by weight and 80% by weight, respectively, compared to 66.5% by weight for methanol when fresh catalyst is used. 1-butanol provides much higher butylene selectivities. A significant amount of propylene is also produced. The alcohol contacted catalyst is then directed to the methanol conversion. reactor resulting in improved methanol conversion and greater ethylene, propylene, and/or butylene productivity.

TABLE 1

|  | Methanol | Ethanol | I-propanol | I-butanol |
|---|---|---|---|---|
| Conversion | 98.2 | 100 | 99.03 | 99.31 |
| Methane selectivity, C | 1.43 | 0.04 | 0.03 | 0.03 |
| Ethylene selectivity, $C_2^=$ | 25.32 | 99.0 | 1.47 | 1.19 |
| Ethane selectivity, $C_2$ | 0.23 | 0.12 | 0.02 | 0.02 |
| Propylene selectivity, $C_3^=$ | 41.18 | 0.22 | 78.70 | 23.64 |
| Propane selectivity, $C_3$ | 0 | 0 | 0 | 0 |
| Butanes selectivity, $C_4$ | 0.65 | 0.05 | 0.18 | 1.03 |
| Butylenes selectivity, $C_4^=$ | 15.53 | 0.44 | 11.06 | 55.84 |
| $C_5^+$ selectivity | 15.66 | 0.13 | 8.44 | 18.25 |
| $C_2^=$ plus $C_3^=$ selectivity | 66.50 | 99.22 | 80.26 | 24.83 |

Having now fully described this invention, it will be appreciated by those skilled in the art that the invention can be performed within a wide range of parameters within what is claimed, without departing from. the spirit and scope of the invention.

What is claimed is:

1. A method of making a product containing olefin comprising:
    contacting, in an oxygenate conversion zone, a catalyst incorporating a silicoaluminophosphate molecular sieve, a metal containing silicoaluminophosphate molecular sieve, or mixtures thereof with an oxygenate to convert a portion of the oxygenate to an olefin product;
    separating the catalyst from the olefin product and directing a portion of the separated catalyst to a regenerator;
    contacting, in an alcohol contact zone, the regenerated catalyst with method and an alcohol, selected from the group consisting of ethanol, 1-propanol, 1-butanol, and mixtures thereof; and
    directing the alcohol contacted catalyst from the alcohol contact zone to the oxygenate conversion zone.

2. The method of claim 1 wherein the alcohol comprises 1% to 99% by weight ethanol.

3. The method of claim 1 wherein the alcohol comprises 1% to 60% by weight methanol and 40% to 99% by weight ethanol.

4. The method of claims 1 wherein the alcoholcomprises 1% to 99% by weight 1-propanol.

5. The method of claim 1 wherein the alcohol comprises 1% to 60% by weight methanol and 40% to 99% by weight 1-propanol.

6. The method of claim 1 wherein the alcohol comprises 1% to 99% by weight 1-butanol.

7. The method of claim 1 wherein the alcohol comprises 1% to 60% by weight methanol and 40% to 99% by weight 1-butanol.

8. The method of claim 1 wherein the alcohol comprises at least 20% by weight ethanol, at least 10% by weight 1-propanol, and the remaining percent by weight methanol.

9. The method of claim 8 wherein the alcohol comprises at least 40% by weight ethanol, at least 10% by weight 1-propanol, and the remaining percentby weight methanol.

10. The method of claim 1 wherein the alcohol comprises at least 20% by weight ethanol, at least 20% by weight 1-propanol, at least 10% by weight butanol, and the remaining.percent by weight methanol.

11. The method of claim 1 wherein the alcohol comprises at least 20% by weight ethanol, at least 20% by weight 1-butanol, and the remaining percent by weight methanol.

12. The method of claim 1 wherein the molecular sieve catalyst contains SAPO molecular sieve selected from the group consisting of SAPO-5, SAPO-17, SAPO-18, SAPO-20, SAPO-34, SAPO-44, SAPO-56, the metal containing forms of each thereof, or mixtures thereof.

13. The method of claim 1 wherein contacting the regenerated catalyst with the alcohol comprises contacting the catalyst at a temperature from 350° C. to 550° C.

14. The method of claim 1 further comprising directing fresh catalyst-to the alcohol contact zone, wherein the fresh catalyst contacts the alcohol.

15. The method of claim 1 wherein the oxygenate comprises methanol.

16. The method of claim 1 wherein the alcohol contact zone is an auxiliary reactor.

17. The method of claim 1 further comprising separating hydrocarbon produced in the alcohol contact zone from the alcohol contacted catalyst.

18. The method of claim 1 wherein contacting the regenerated catalyst with the alcohol comprises adding from about 2% to about 60% by weight $CH_2$ per weight of catalyst.

19. The method of claim 18 wherein contacting the regenerated catalyst with the alcohol comprises adding from about 2% to about 20% by weight $CH_2$ per weight catalyst.

20. A method of making a product containing olefin comprising:
    contacting, in an oxygenate conversion zone, a molecular sieve catalyst with an oxygenate to convert a portion of the oxygenate to an olefin product;
    separating the catalyst from the olefin product and directing a portion of the separated catalyst to a regenerator;
    contacting, in an alcohol contact zone, the regenerated catalyst with methanol and an alcohol, selected from the group consisting of ethanol, 1-propanol, 1-butanol, and mixtures thereof; and
    directing the alcohol contacted catalyst from the alcohol contact zone to the oxygenate conversion zone.

21. The method of claim 20, wherein the alcohol comprises 1% to 60% by weight methanol and 40% to 99% by weight ethanol.

22. The method of claim 20, wherein the alcohol comprises 1% to 60% by weight methanol and 40% to 99% by weight 1-propanol.

23. The method of claim 20, wherein the alcohol comprises 1% to 60% by weight methanol and 40% to 99% by weight 1-butanol.

24. The method of claim 20, wherein the alcohol comprises at least 20% by weight ethanol, at least 10% by weight 1-propanol, and the remaining percent by weight methanol.

25. The method of claim 24, wherein the alcohol comprises at least 40% by weight ethanol, at least 10% by weight 1-propanol, and the remaining percent by weight methanol.

26. The method of claim 20, wherein the alcohol comprises at least 20% by weight ethanol, at least 20% by weight 1-propanol, at least 10% by weight butanol, and the remaining percent by weight methanol.

27. The method of claim 20, wherein the alcohol comprises at least 20% by weight ethanol, at least 20% by weight 1-butanol, and the remaining percent by weight methanol.

* * * * *

UNITED STATES PATENT AND TRADEMARK OFFICE
CERTIFICATE OF CORRECTION

PATENT NO.    : 6,441,262 B1
DATED         : August 27, 2002
INVENTOR(S)   : Shun C. Fung and Chunshe Cao It is certified that error appears in the above-identified patent and that said Letters Patent is hereby corrected as shown below:

<u>Column 13,</u>
Line 46, replace "method" with -- methanol --.

Signed and Sealed this

Twenty-seventh Day of January, 2004

JON W. DUDAS
*Acting Director of the United States Patent and Trademark Office*